US009952244B2

(12) United States Patent
Berberich et al.

(10) Patent No.: US 9,952,244 B2
(45) Date of Patent: Apr. 24, 2018

(54) DEVICE AND METHOD FOR HANDLING RACKS OF DISPOSABLE PIPETTE TIPS IN A LABORATORY AUTOMATION SYSTEM AND LABORATORY AUTOMATION SYSTEM

(71) Applicant: Roche Diagnostics Operations, Inc., Indianapolis, IN (US)

(72) Inventors: Walter Berberich, Kirchheim/Teck (DE); Julian Baumgart, Backnang (DE); Richard-Paul Daisley, Stuttgart (DE); Dominik Strzempek, Kernen (DE); Stefan Soentges, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/182,900

(22) Filed: Jun. 15, 2016

(65) Prior Publication Data
US 2016/0377643 A1 Dec. 29, 2016

(30) Foreign Application Priority Data
Jun. 25, 2015 (EP) .................................... 15173748

(51) Int. Cl.
*G01N 35/04* (2006.01)
*G01N 35/10* (2006.01)
(Continued)

(52) U.S. Cl.
CPC .............. *G01N 35/10* (2013.01); *B01L 9/543* (2013.01); *G01N 35/02* (2013.01); *G01N 35/04* (2013.01);
(Continued)

(58) Field of Classification Search
CPC ........ B65G 1/026; B65G 60/00; B65G 65/00; G01N 35/04; G01N 2035/0425; B01L 9/543; B23Q 7/1442
(Continued)

(56) References Cited

U.S. PATENT DOCUMENTS 5,190,434 A * 3/1993 Miura .................... B23P 19/001
414/416.11
5,207,727 A * 5/1993 Pearce .................... B65B 5/068
206/443
(Continued)

FOREIGN PATENT DOCUMENTS

EP 0753749 A1 1/1997
EP 2210668 A2 7/2010
(Continued)

*Primary Examiner* — Gregory W Adams
(74) *Attorney, Agent, or Firm* — Roche Diagnostics Operations, Inc.

(57) ABSTRACT

A device and method for handling racks of disposable pipette tips in a laboratory automation system are presented. The device comprises a guide rail for guiding racks from a loading region (I) to a supply region (II). The loading region (I) is accessible by a user or a loading device for loading a rack on the guide rail. A plurality of disposable pipette tips stored in a supplying rack located in the supply region (II) is accessible by a delivering device for delivering at least one selected one of the plurality of disposable pipette tips to a pipetting system. The device comprises at least one moveable element, which is controllably moveable by a driving device for selectively enabling or disabling a removal of the supplying rack from the supply region (II). A laboratory automation system comprising such a device and/or for carrying out the method are also presented.

16 Claims, 4 Drawing Sheets

(51) Int. Cl.
*G01N 35/02* (2006.01)
*B01L 9/00* (2006.01)
*G01N 35/00* (2006.01)

(52) U.S. Cl.
CPC .............. *G01N 2035/00277* (2013.01); *G01N 2035/0465* (2013.01)

(58) Field of Classification Search
USPC ..... 414/222.08, 222.1, 222.11, 749.1, 751.1, 414/788.7, 792.7, 793.4, 794.2, 794.3, 414/794.7, 794.8, 795.6; 422/62, 65; 74/89.21
See application file for complete search history.

(56) References Cited

U.S. PATENT DOCUMENTS

| | | | | |
|---|---|---|---|---|
| 5,470,193 | A * | 11/1995 | Miura | B23Q 7/1447 414/331.04 |
| 5,882,174 | A * | 3/1999 | Woerner | B65G 65/00 414/788.7 |
| 6,426,044 | B1 * | 7/2002 | Cohen | G01N 35/04 422/105 |
| 6,586,255 | B1 * | 7/2003 | Hubert | G01N 35/0099 422/504 |
| 7,360,984 | B1 * | 4/2008 | Sugiyama | B01L 9/543 414/798.1 |
| 7,448,487 | B2 * | 11/2008 | Koike | G01N 35/026 198/349 |
| 7,578,383 | B2 * | 8/2009 | Itoh | G01N 35/04 198/468.01 |
| 2009/0191095 | A1 * | 7/2009 | Nakamura | G01N 35/026 422/67 |
| 2013/0195720 | A1 * | 8/2013 | Behnk | B65G 49/00 422/68.1 |
| 2013/0307381 | A1 * | 11/2013 | Itoh | G01N 35/04 312/97 |

FOREIGN PATENT DOCUMENTS

| | | |
|---|---|---|
| EP | 2620776 A1 | 7/2013 |
| EP | 2803412 A2 | 11/2014 |

* cited by examiner

DEVICE AND METHOD FOR HANDLING RACKS OF DISPOSABLE PIPETTE TIPS IN A LABORATORY AUTOMATION SYSTEM AND LABORATORY AUTOMATION SYSTEM

CROSS-REFERENCE TO RELATED APPLICATIONS

This application is a continuation of EP 15173748.3, filed Jun. 25, 2015, which is hereby incorporated by reference.

BACKGROUND

The present disclosure relates to a device and method for handling racks of disposable pipette tips in a laboratory automation system.

A typical laboratory automation system comprises at least one pre-analytical, analytical and/or post-analytical station, in which samples, for example blood, saliva, swab and other specimens taken from the human body or plant materials, are processed. It is well known to provide pipetting systems using disposable pipette tips, which are attached to a main body of a pipetting device and replaced after each use or when required. Typically, racks are provided, which are configured to store a predetermined number of pipette tips of a certain size and with a defined spacing. The racks are also referred to as trays or magazines. The racks are presented to a gripper or any other delivery system for delivering the tips to the pipetting system.

It is known to provide a laboratory automation system using disposable pipette tips with drawers. A number of racks is loaded into or on an extracted drawer and the drawer is moved into a use position for allowing a pipetting system to use the disposable pipette tips. For using the disposable pipette tips, for example, a gripper is driven to move to the individual positions of the disposable tips held by each rack and to pick up the pipette tips one after the other. After all pipette tips are used, the drawer is ejected and the empty racks are manually removed and replaced.

Therefore, there is a need for an improved device and method for handling racks of disposable pipette tips in a laboratory automation system.

SUMMARY

According to the present disclosure, a device for handling racks of disposable pipette tips in a laboratory automation system is presented. The device can comprise at least one guide rail for guiding racks from a loading region (I) to a supply region (II). The loading region (I) can be accessible by a user or a loading device for loading at least one rack on the at least one guide rail. A plurality of disposable pipette tips stored in a supplying rack located in the supply region (II) can be accessible by a delivering device for delivering at least one selected one of the plurality of disposable pipette tips to a pipetting system. The device can also comprise at least one moveable element, which can be controllably moveable by a driving device for selectively enabling or disabling a removal of the supplying rack from the supply region (II).

Accordingly, it is a feature of the embodiments of the present disclosure to provide for an improved device and method for handling racks of disposable pipette tips in a laboratory automation system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
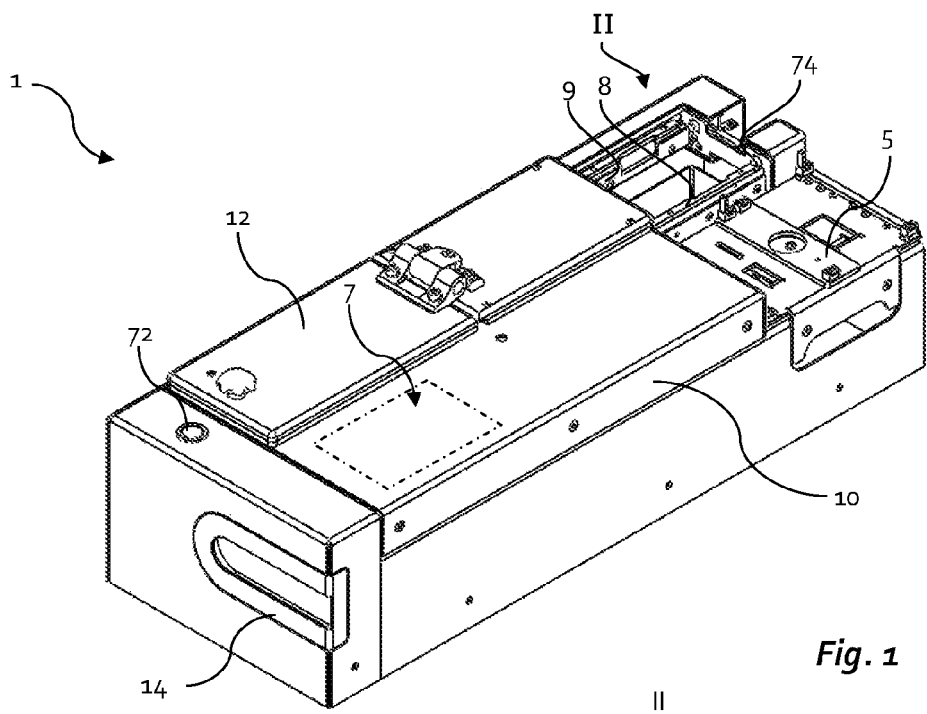
FIG. 1 illustrates a perspective view of the device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for handling racks of disposable pipette tips in a laboratory automation system is provided. The device can comprise at least one guide rail for guiding racks from a loading region to a supply region. The loading region can be accessible by a user or a loading device for loading at least one rack on the at least one guide rail. A plurality of disposable pipette tips stored in a supplying rack located in the supply region can be accessible by a delivering device for delivering at least one selected one of the plurality of disposable pipette tips to a pipetting system. The device can comprise at least one moveable element, which can be controllably moveable by a driving device for selectively enabling or disabling a removal of the supplying rack from the supply region.

A driving device can be assigned to the moveable element. The moveable element can be moveable in a controllable manner by the driving device. The moveable element can be driven to move in at least one direction by the driving device. In one embodiment, a return motion can also be effected by the driving device. In other embodiments, the return motion can be effected by a passive element, such as a return spring. The controllably moveable element can be brought into a first position, in which the supplying rack can be supported and/or secured, for example, clamped, in the supply region during a delivery of the tips. A removal from the supply region can be disabled during the delivery. After the rack is empty and before placing a new rack in the supply region, the moveable element can be moved to a second position to release the supplying rack in a reliable and repeatable manner.

In some embodiments, the driving device can be adapted to effect a to-and-fro movement of the at least one moveable element. The to-and-fro movement can allow for a removal of the supplying rack even in case the supplying rack sticks to walls at the supply region, for example, to a wall of the moveable element. In some embodiments, the driving device can comprise a solenoid to produce a fast to-and-fro movement of the moveable element. In some embodiments, activating of the driving device can be controlled or triggered by a control device. The control device, in some embodiments, can be integrated and/or in communication with a central control device of the laboratory automation system having information about an emptying state of the supplying rack.

The rack can be moved in a movement direction along the at least one guide rail into the supply region. In one embodiment, the controllably moveable element can be a moveable wall element arranged substantially perpendicular to the movement direction. The wall element can be moved out of the movement path for a removal of the racks in the movement direction.

In some embodiments, the device can be arranged for a removal of the supplying rack from the supply region in a direction substantially transverse to the movement direction of the rack along the at least one guide rail. In other words, a movement direction for moving a rack into the supply region can differ from the movement direction for moving a rack out of the supply region. In such an embodiment, a plurality of racks can be successively moved into the supply region. Removing a supplying rack in a direction transverse to the movement direction can be carried out prior to moving a successive rack into the supply region. In some embodiments, the movement direction along the at least one guide rail can lie in a horizontal plane (within working tolerances) in order to avoid an influence of gravitational forces when moving the racks in the movement direction. In one embodiment, the supplying rack can be removed in a downward direction. Hence, for a removal of the supplying rack advantage can be taken of gravitational forces.

In one embodiment, at least one moveable block can be provided as the controllably moveable element. The at least one moveable block can be moveable between a support position and a release position. At the supply region, the supplying rack can be placed on the at least one moveable block arranged in the support position and the at least one moveable block can be moved into the release position for a removal of the supplying rack from the supply region in a downward direction. In the support position, the moveable block can extend the at least one guide rail in the longitudinal direction of the guide rail. Thereby, a smooth transition of the supplying rack from the guide rail to the moveable block can be ensured. The moveable block can be provided with a side surface acting against the supplying rack when the at least one moveable block is in the support position. The side surface can allow a clamping of the supplying rack in the supply region.

The empty racks can be collected in a container. In some embodiments, a chute can be provided underneath the supply region. The device can be arranged for a removal of the supplying rack via the chute.

In some embodiments, at the supply region, at least one abutment surface can be provided substantially perpendicular to the movement direction of the rack along the at least one guide rail. By the abutment surface, the supplying rack can be positioned at the supply region in a repeatable manner and with high accuracy. This can allow for a reliable pick-up or gripping of the disposable pipette tips by a delivering device.

In some embodiments, a pusher can be provided. The supplying rack can be forced against the abutment surface by the pusher. The pusher can be adapted to be driven to and fro. The pusher can be moved away from the supplying rack in order to release the supplying rack and remove the supplying rack from the supply region.

In one embodiment, the pusher can be distinct from a moving device for moving the racks along the guide rails. In some embodiments, the pusher can be moveable between a home position and a working position for moving the rack from the loading region to the supply region. In other words, the pusher can have two functions and can be driven to move a rack from a loading region to a supply region or to secure a supplying rack in the supply region by forcing the supplying rack against the abutment surface.

In one embodiment, one rack can be placed on the at least one guide rails at the time and a subsequent rack can be placed on the at least one guide rail after a removal of the rack. In some embodiments, the at least one guide rail can be adapted to receive a plurality of racks. A rack moving mechanism can be provided for moving the racks one by one towards and/or into the supply region. The pusher for securing the supplying rack at the supply region in some embodiments can be integrated in the rack moving mechanism.

In some embodiments, the device can be a drawer unit comprising a drawer module. The drawer module can be moveable between a use position and an eject position. In the eject position, an access to the loading position can be facilitated allowing the device to be isolated from an environment when arranged in a use position.

In some embodiments, at least one sensor can be provided for detecting a removal of the supplying rack from the supply region, a presence of the supplying rack in the supply region, a state of the rack moving mechanism, a state or position of the drawer module and/or a state of an openable window provided at a cover of the device. The at least one sensor can communicate with a control device assigned to the device and/or a central control device of the laboratory automation system.

A method for handling racks of disposable pipette tips in a device for a laboratory automation system is provided. The device can comprise at least one guide rail for guiding racks from a loading region to a supply region. The method can comprise: (a) placing a rack at the loading region on the at least one guide rail, (b) moving the rack along the at least one guide rail into the supply region, wherein a plurality of disposable pipette tips stored in the rack located in the supply region is accessible by a delivering device for delivering at least one selected one of the plurality of disposable pipette tips to a pipetting system, (c) securely positioning and holding the rack in the supply region, while delivering at least one selected one of the plurality of disposable pipette tips to a pipetting system, and (d) activating a driving device assigned to at least one moveable element for moving the at least one moveable element into a release position for releasing the rack and for a removal of the rack from the supply region.

After the moveable element is moved into the release position, in one embodiment, a pusher can be driven to move the rack out of the supply region.

In some embodiments, the moveable element can be a moveable block, which can be controlled to move between a support position and a release position. At the supply region, the rack can be placed on the at least one moveable block arranged in the support position and the at least one moveable block can be moved into the release position for a removal of the rack from the supply region in a downward direction due to gravity.

In alternative or in addition, in one embodiment, at the supply region the rack can be forced against at least one abutment surface. The abutment surface can be arranged substantially perpendicular to the movement direction of the rack along the at least one guide rail. The rack can be forced against the abutment surface by the pusher. A wall comprising the abutment surface, in one embodiment, can be moved to a release position for releasing the rack. In some embodiments, the abutment surface can be arranged at a wall which can be fixed in position with respect to the guide rails.

A laboratory automation system with at least one of pre-analytical, analytical and/or post-analytical station with a pipetting system is provided.

FIGS. 1 to 8 show an embodiment of a device 1 for handling racks 2 of disposable pipette tips 20 in a laboratory automation system. The device 1 can be provided with a cover 10 having an openable window 12. The device 1 can further comprise a grip recess 14, the purpose of which will be explained further below.

Figure 2:
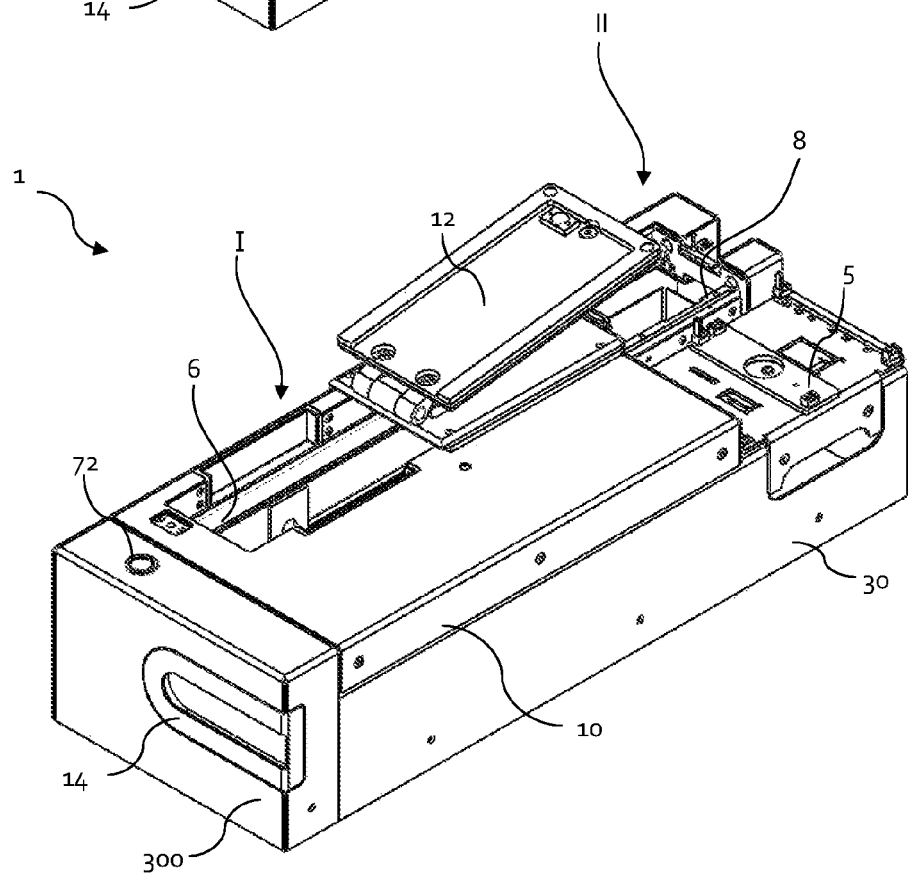
FIG. 2 illustrates a perspective view of the device of FIG. 1 upon loading according to an embodiment of the present disclosure.
Figure 3:
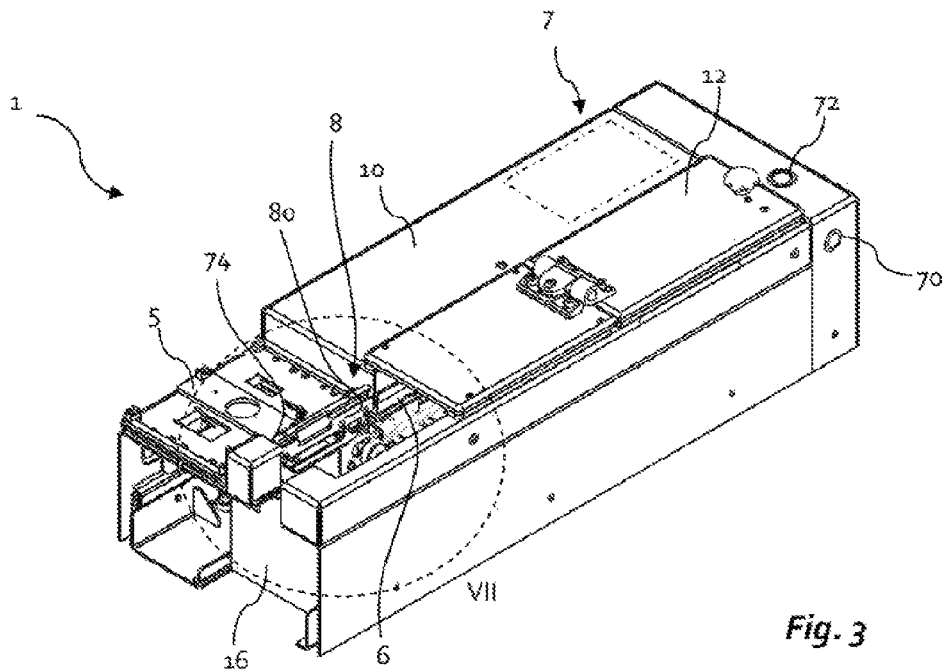
FIG. 3 illustrates a perspective view of the device of FIG. 1 from the back according to an embodiment of the present disclosure.

FIGS. 1 and 2 are perspective views of the device 1. In FIG. 1, the window 12 is closed and, in FIG. 2, the window 12 is open for loading the device 1. FIG. 3 is a perspective view of the device 1 from behind. As can be seen in FIGS. 1 and 3, the device 1 can comprise two guide rails 6 for slideably receiving a plurality of racks 2 of disposable pipette tips 20 (see FIG. 5). Only one guide rail 6 is visible in each of FIGS. 1 and 3. In the embodiment shown, a maximum of four racks 2 can be placed on the guide rails 6. The guide rails 6 shown are optimized for receiving racks 2 as known in the art. However, other racks 2 can be placed on the guide rails 6 and/or the guide rails 6 can be designed for receiving other types of racks.

The guide rails 6 can be arranged for guiding a rack 2 placed thereon from a loading region I to a supply region II.

For allowing access to the guide rails 6, the window 12 can be opened as shown in FIG. 2. After the window 12 is opened, the loading region I can be accessible by a user or a loading device for placing at least one rack 2 on the guide rails 6.

Figure 5:
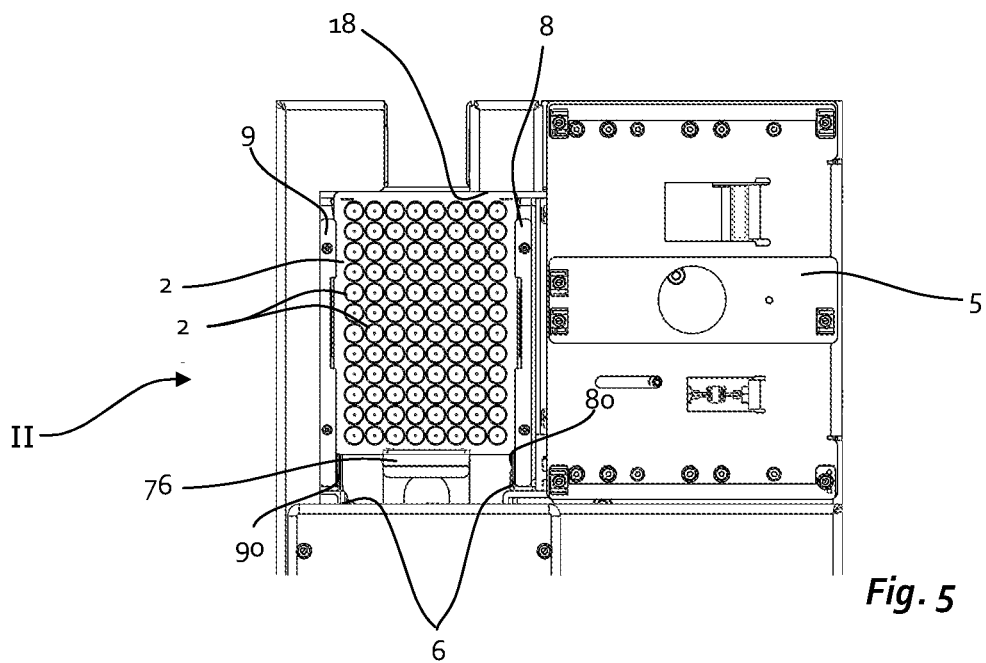
FIG. 5 illustrates a top view of detail of the device of FIG. 1 with a rack secured in a supply region according to an embodiment of the present disclosure.

The racks 2 can be provided with a plurality of disposable pipette tips 20 (as shown in FIG. 5). The disposable pipette tips 20 stored in the rack 2 can be accessible when the rack 2 is arranged at the supply region II by a delivering device such as, for example, a gripper, for delivering the plurality of disposable pipette tips 20 one by one to a pipetting system. Adjacent to the supply region II, a holder 5 for a microwell or microtiter plate can be provided.

The device 1 can comprise a rack moving mechanism 7 arranged underneath the cover 10. The rack moving mechanism 7 can be provided with an element engaging with the racks 2 for successively moving the racks 2 from the loading region I into the supply region II.

In the embodiment shown, the racks 2 can be loaded one at the time. After placing one rack 2 on the rails 6, the rack moving mechanism 7 can be activated by pressing a rack loader button 70 (see FIG. 3) for moving the rack 2 towards the supply region II. An optical element such as, for example, an LED light 72 can indicate that the device 1 is ready for loading a subsequent rack 2. Opening the window 12 can be hindered while the device 1 is not ready for loading.

A sensor 74 can be provided for sensing the presence of a rack 2 in the supply region II.

The guide rails 6 may not reach into the supply region II. Rather, the guide rails 6 can be extended by a pair of blocks 8, 9. The supplying rack 2 can rest on the blocks 8, 9 in the supply region II. At least one of the blocks 8, 9 can be a moveable block 8, which can be moveable between a support position and a release position. In the case the moveable block 8 is in the support position, as shown in FIG. 3, the moveable block 8 can be arranged in the extension of a guide rail 6 and the supplying rack 2 moved into the supply region II can be placed on the moveable block 8. By a driving device 82 (see FIG. 4), the moveable block can be moved into the release position. The distance of the moveable block 8 from the other block 9 can be larger than the width of the rack 2 so that the rack 2 can fall downwards due to gravity. In the embodiment shown, the moveable block 8 and the second block can be provided with side surface 80, 90 acting against the supplying rack 2 when the moveable block 8 is in the support position so that the supplying rack 2 can be precisely positioned between the two blocks 8, 9, when the moveable block 8 is in the support position.

Figure 4:
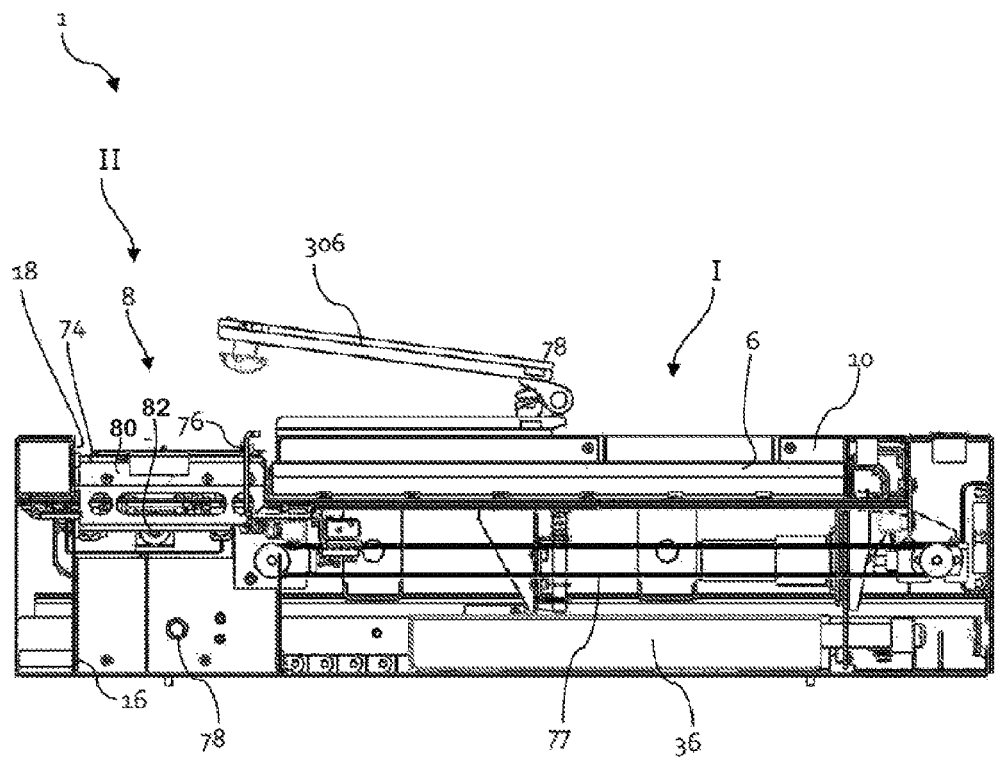
FIG. 4 illustrates a sectional side of the device of FIG. 1 according to an embodiment of the present disclosure.

FIG. 4 is a sectional side view of the device of FIG. 1, wherein the window 12 is open. As shown in FIG. 4 the depicted rack moving mechanism 7 can comprise a pusher 76 for pushing the racks 2 towards the supply region II. In FIG. 4, the pusher 76 is positioned in a working position. The working position can be close to the supply region II and the device 1 may not be ready for loading. The pusher 76 can be moved into or towards the work position for forcing a supplying rack 2 against an abutment surface 18. The abutment surface 18 can be provided substantially perpendicular to the movement direction of the supplying rack 2 along the guide rails 6.

For loading the device 1, the pusher 76 can be moved beyond the loading region I away from the supply region II into a home position. When the pusher 76 is in the home position, a rack 2 can be positioned between the supply region II and the pusher 76 and can be moved by the pusher 76 into the supply region II. For moving the pusher 76, in the depicted embodiment, a belt drive 77 can be provided. The rack moving mechanism 7 can further comprise a motor and hardware and/or software for a motor drive condition monitoring, for monitoring, for example, over current, drive slippage, belt slippage or belt derailment, motor blockage. The driving device 82 for moving the moveable block 8 between the support position and the release position can be either integrated into the rack moving mechanism and/or in communication with the rack moving mechanism 7 for a coordination of a movement of all elements.

Underneath the supply region II, a chute 16 can be provided. The device 1 can allow for an automated removal of the racks 2 from the supply region II via the chute 16. A successful removal can be observed by a sensor 78 such as, for example, an ultrasound sensor. After a successful removal, a successive rack within the device 1 can be moved by the rack moving mechanism 7 into the supply region II. In case the device 1 is empty, an operator or user can be prompted to refill the device.

Figure 7:
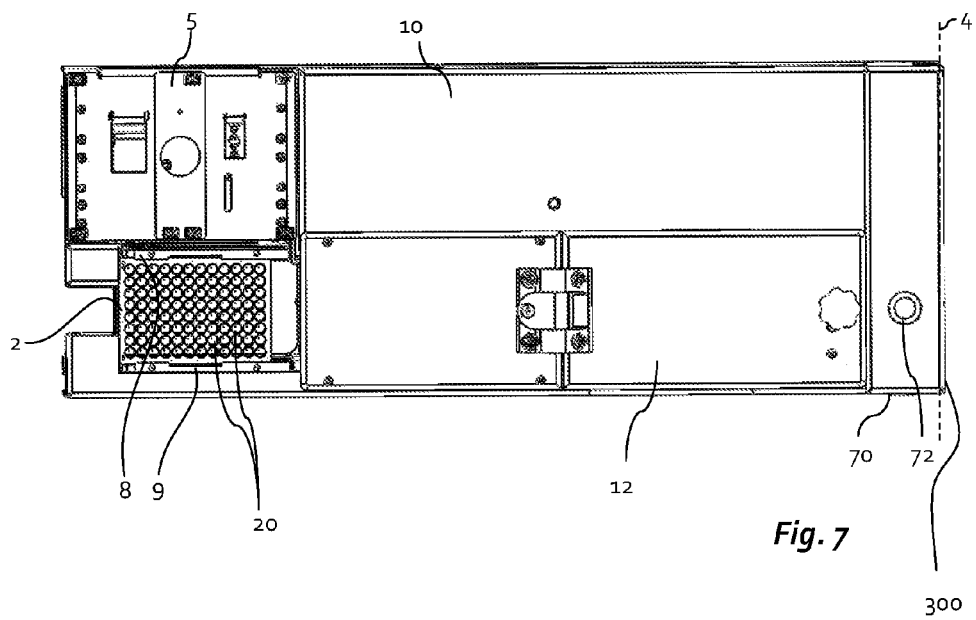
FIG. 7 illustrates top view of the device of FIG. 1 device for handling racks in a use position according to an embodiment of the present disclosure.

Further, an ejector device 36 can be provided, the function of which is discussed further below with reference to FIGS. 7 and 8.

Figure 6:
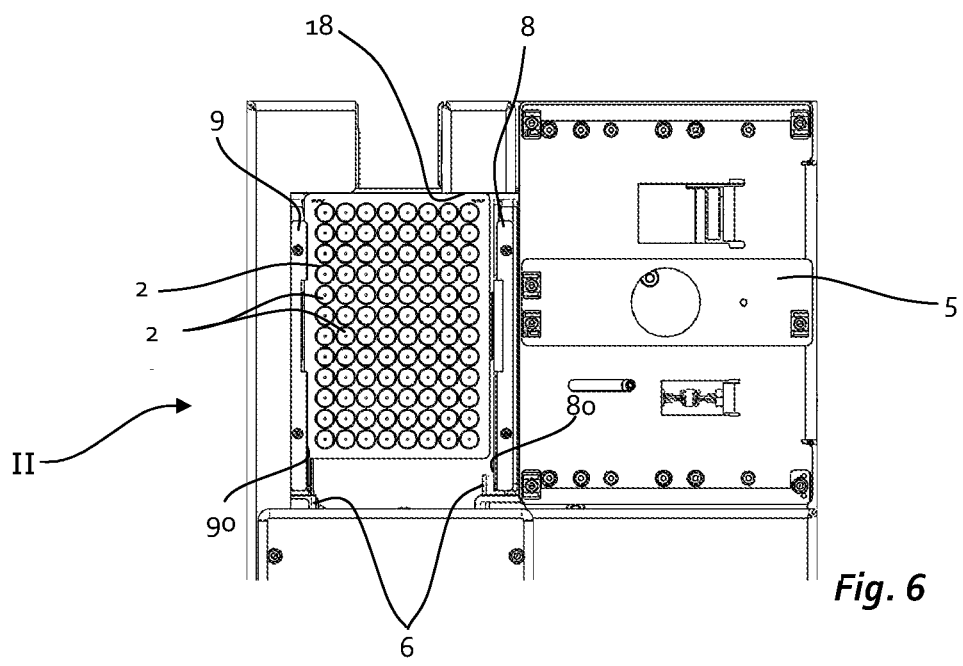
FIG. 6 illustrates a top view of the detail of the device of FIG. 1 shown in FIG. 5 with a rack prior to a removal of the rack according to an embodiment of the present disclosure.

FIGS. 5 and 6 are top views of a detail of the device of FIG. 1 showing the supply region II with a rack 2 secured in the supply region II and with the rack 2 unsecured for a removal, respectively. As can be seen in FIGS. 5 and 6, the guide rails 6 can be extended by two blocks 8, 9 on which the rack 2 can rest in the supply region II. The block 8 adjacent to the holder 5 for the microwell plate can be a moveable block 8. The second block 9 can be mounted fixed in position. In other embodiments, both blocks can be moveable. In still another embodiment, only one guide rail 6 can be extend by a moveable block 8, whereas the other guide rail 6 can reach into the region of the supply region II. The blocks 8, 9 can be provided with side walls 89, 90 contacting the rack 2 so that the rack 2 can be securely positioned and held in the supply region II. At an end of the region of the supply region II opposite the guide rails 6, an abutment surface 18 can be provided substantially perpendicular to a movement direction of the rack 2 along the guide rails 6. As shown in FIG. 5, the rack 2 can be forced against the abutment surface 18 and thereby secured in the supply region II by the pusher 76.

Once the rack 2 is ready for a removal, the moveable block 8 and the pusher 76 can be moved away from the rack 2 to release the rack 2. In the embodiment shown, only the moveable block 8 adjacent to the holder 5 for the microwell plate is moved, allowing for a simplified drive mechanism for the moveable block 8. In one embodiment, a block driving device such as, for example, a solenoid can be provided for moving the block 8 back and forth. An activation or deactivation of the solenoid can be controlled by a control device of the rack moving mechanism 7.

In one embodiment, the guide rails and the racks can be provided with a nut and groove connection for a reliable guidance of the racks along the guide rails 2. However, the blocks 8, 9 can support the racks without any form-locking transverse to the movement direction along the guide rails in order to allow for a relative movement of the moveable block in this direction for a removal of the racks.

In the embodiment shown, the device 1 can be a drawer unit. As shown in FIGS. 7 and 8, the drawer unit can comprise a drawer module 30 slideably supported on a base plate 32 by drawer rails 34. The drawer module 3 can be moveable with respect to the base plate 4 between a use position shown in FIG. 7 and an eject position shown in FIG. 8. The device 1 can be integrated into a laboratory automation system. In the use position, a front end 300 of the drawer module 30 can be flush with or behind a front wall 4 (schematically shown by a broken line in FIGS. 7 and 8) of a housing of the laboratory automation system and the interior of the device 1 may not be accessible. The supply region II (see FIGS. 1 to 6) can be located in the region of a rear end of the drawer module 30 opposite the front end 300.

The base plate 32 can be fixed to the housing of the laboratory automation system or integrally formed with a wall of the housing. A grip recess 14 (see FIG. 3) for manually moving the drawer module 30 with respect to the base plate 32 can be provided at the front end 300. In addition, an ejector device 36 can be provided. In practice, the drawer module 30 can be locked in the use position shown in FIG. 7. In order to allow a transfer of the drawer module 30 into the eject position, the ejector device 36 can be activated and the drawer module 30 can be moved towards the eject position. The ejector device 36 can move the drawer module 30 only over a small distance. A further movement of the drawer module 30 into the eject position shown in FIG. 8 can be carried out manually by user.

The chute 16 can be provided at the base plate 32. The chute 16 can be arranged underneath the supply region when the drawer module 30 is moved to the use position. When moving the drawer module 30 into the use position, the rack moving mechanism 7 can force the rack 2 or the racks 2 loaded towards the supply region II (see FIG. 5) to ensure that the first one of the racks 2 is in the correct position. For moving the drawer module 30 into the use position, the window 12 may need to be closed. In one embodiment, the rack moving mechanism 7 can only be activated if the window 12 is closed.

In the following, a use of the device 1 is described. The device 1 can be incorporated in a laboratory automation system such as, for example, in an automatic aliquoter used to transfer an aliquot of a sample to a microwell or microtiter plate.

On turning on the laboratory automation system including the device 1, the pusher 76 can move towards the supply region II for securing a rack 2 in the supply region II as shown in FIG. 5. In the case there are no racks 2 loaded in the device 1, the pusher 76 can travel in the opposite direction, towards its home position. The information that the device 1 is empty can be transmitted to a central control unit of the laboratory automation system. The user can then be prompted to load the device with fully stocked racks 2.

Figure 8:
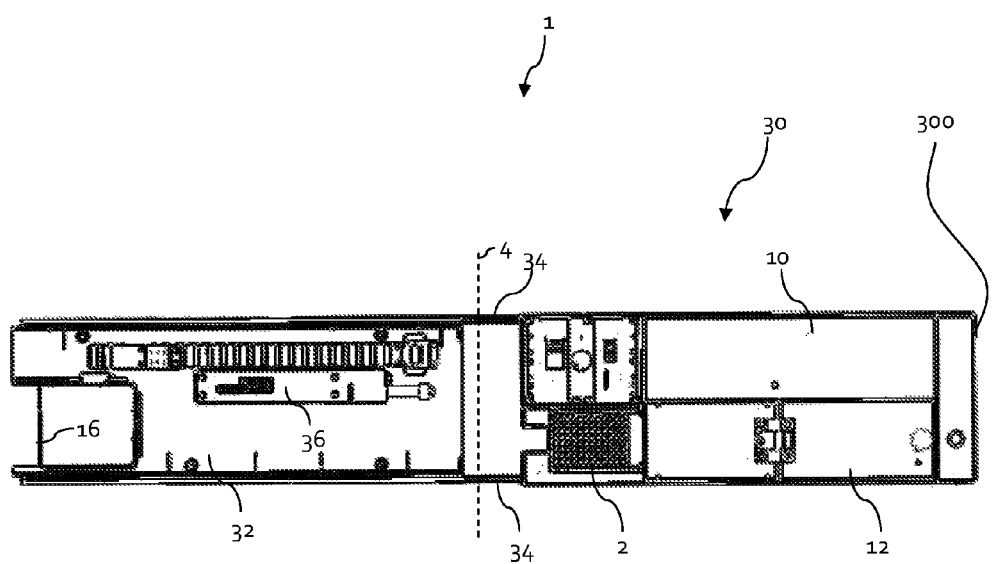
FIG. 8 illustrates top view of the device of FIG. 1 in an eject position according to an embodiment of the present disclosure.

Next, the drawer module 30 can be moved into the eject position shown in FIG. 8 providing the user with an ergonomically friendly access to the device 1. In some embodiments, the transfer can be carried out semi-automatically when starting the device 1 in an empty state, after a removal of the last rack 2 and/or after the operator or user has pressed a respective button. The ejector device 36 can push the drawer module over a small distance towards the eject position for releasing the drawer module 30 from a locked state. A subsequent movement into the eject position can be carried out manually by an operator or user. In other embodiments, the transfer into the eject position can be carried out fully automatically by the ejector device 36. In still another embodiment, the full movement can be carried out manually.

When the drawer unit 30 is in the eject position and the pusher 76 is in the home position, the window 12 can be opened as shown in FIG. 2 and the racks 2 can be loaded. The racks 2 can be loaded one at a time and can be pushed into an appropriate position by closing the window 12 and then activating the pusher 76 by pressing the rack loader button 70. The pusher 76 can push the rack or the plurality of racks loaded towards the supply region and can travel back into the home position. After the pusher 76 has reached the home position, the LED light 72 can indicate that the device 1 is ready for loading a subsequent rack 2.

After the desired number of racks 2 is loaded, the drawer module 30 can be transferred to the use position. In the embodiment shown, a maximum of four racks 2 can be loaded. When moving the drawer module 30 into the use position, the pusher 76 can travel towards the supply region II moving the rack 2 or the plurality of racks 2 until a first one of the racks 2 reaches the supply region II and activates the sensor 74. The rack 2 can be secured in the supply region II as shown in FIG. 5. This information can be sent to a central control unit of the laboratory automation system for informing the system that a rack 2 is located in the supply region II and that the device 1 is ready for the tip placement process.

The disposable pipette tips 20 can be used one after the other and disposed after use until the rack 2 is empty. A removal of an empty rack 2, in some embodiments, can be triggered by the central control unit of the laboratory automation system, which can detect that all pipette tips 20 have been used and can send a respective signal to a device control unit of the device 1.

The device 1 can then release the rack 2 by moving the pusher 76 and the at least one moveable block 8 away from the rack 2 as shown in FIG. 6. At first, the pusher 76 can be activated to travel away from the supply region II towards its home position over a short distance, for example, over a distance of approximately 10 to 30 mm. This may also cause a small movement of the rack 2 towards the home position of the pusher 76. Next, the moveable block 8 can be driven to move a number of times to and fro between the positions shown in FIGS. 5 and 6, for example, about three to six times, to cause the rack 2 to fall into the chute 16 and via the chute 16 into a waste container located underneath. The removal of the rack 2 via the chute 16 can be detected by the sensor 78. After a successful removal of a rack 2 from the supply region II, the pusher 76 can be driven to move a subsequent rack 2 into the supply region II. This can be repeated until the device 1 is empty and the user is prompted to refill the device 1.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for handling racks of disposable pipette tips in a laboratory automation system, the device comprising:
   a loading region (I);
   a supply region (II) comprising at least one moveable block;
   at least one guide rail for guiding racks from the loading region (I) along a movement direction lying in a horizontal plane to the supply region (II), wherein a plurality of disposable pipette tips stored in a supplying rack located in the supply region (II) is accessible by a delivering device for delivering at least one selected one of the plurality of disposable pipette tips to a pipetting system, wherein the loading region (I) is accessible by a user or a loading device for loading at least one rack on the at least one guide rail, wherein the at least one moveable blocks extends along the at least one guide rail and is moveable between a support position and a release position, and wherein at the supply region (II), the supplying rack is placed on the at least one moveable block arranged in the support position and the at least one moveable block is moved into the release position for a removal of the supplying rack from the supply region (II) in a downward direction, and wherein the at least one guide rail is adapted to receive a plurality of racks.

2. The device according to claim 1, wherein the driving device is adapted to effect a to-and-fro movement of the at least one moveable element.

3. The device according to claim 2, wherein the driving device comprises a solenoid.

4. The device according to claim 1, wherein the moveable block is provided with a side surface acting against the supplying rack when the at least one moveable block is in the support position.

5. The device according to claim 1, further comprising,
   a chute provided underneath the supply region (II), wherein the device is arranged for a removal of the supplying rack via the chute.

6. The device according to claim 1, further comprising,
   at the supply region (II), at least one abutment surface perpendicular to the movement direction of the supplying rack along the at least one guide rail.

7. The device according to claim 6, further comprises,
   a pusher, wherein the supplying rack is forced against the abutment surface by the pusher.

8. The device according to claim 7, wherein the pusher is adapted to be driven to and fro.

9. The device according to claim 8, wherein the pusher is moveable to and fro between a home position and a working position for moving the racks from the loading region (I) to the supply region (II) and for releasing the supplying rack.

10. The device according to claim 1, wherein the device is a drawer unit comprising a drawer module moveable between a use position and an eject position.

11. The device according to claim 10, further comprises
    at least one sensor for detecting a removal of the supplying rack from the supply region, a presence of the supplying rack in the supply region (II), a state of the rack moving mechanism, a state of the drawer module and/or a state of an openable window provided at a cover of the device.

12. A method for handling racks of disposable pipette tips in a device for a laboratory automation system, the device comprising at least one guide rail for guiding racks from a loading region (I) to a supply region (II) comprising at least one moveable block, the method comprising:
    placing a rack at the loading region (I) on the at least one guide rail;
    moving the rack along the at least one guide rail into the supply region (II) along a movement direction lying in a horizontal plane, wherein the at least one guide rail receives a plurality of racks, wherein a rack moving mechanism provides for moving the racks one by one towards and/or into the supply region (II), and wherein a plurality of disposable pipette tips stored in the rack located in the supply region (II) is accessible by a delivering device for delivering at least one selected one of the plurality of disposable pipette tips to a pipetting system;
    securely positioning and holding the rack in the supply region (II) while delivering at least one selected one of the plurality of disposable pipette tips to a pipetting system; and
    activating the at least one moveable element to move into a release position for releasing the rack and for a removal of the rack from the supply region (II) in a direction transverse to the movement direction of the rack along the at least one guide rail and wherein the supplying rack is removed in a downward direction.

13. The method according to claim 12, wherein the moveable element is a moveable block controlled to move between a support position and a release position, wherein, at the supply region (II), the rack is placed on at least one moveable block arranged in the support position, and the at least one moveable block is moved into the release position for a removal of the rack from the supply region (II) in a downward direction.

14. The method according to claim 12, further comprising,
   at the supply region (II), forcing the rack against at least one abutment surface, wherein abutment surface is arranged perpendicular to the movement direction of the rack along the at least one guide rail.

15. The method according to claim 14, wherein rack is forced against the abutment surface by a pusher.

16. A laboratory automation system with at least one of pre-analytical, analytical and/or post-analytical station provided with a pipetting system, the laboratory automation system comprising a device according to claim 1 and/or a device adapted for carrying out a method according to claim 12.

* * * * *